United States Patent [19]
Johnson

[11] Patent Number: 6,056,522
[45] Date of Patent: May 2, 2000

[54] REUSABLE CASSETTE WITH A MOVEABLE DOOR

[75] Inventor: Jay Gregory Johnson, Maple Plain, Minn.

[73] Assignee: SIMS Deltec, Inc., St. Paul, Minn.

[21] Appl. No.: 09/076,975

[22] Filed: May 13, 1998

[51] Int. Cl.[7] ................................................. F04B 43/12
[52] U.S. Cl. ...................... 417/474; 604/153; 417/477.2; 417/477.9; 417/479
[58] Field of Search ................................ 417/474, 477.2, 417/479, 477.9, 478; 604/153

[56] References Cited

U.S. PATENT DOCUMENTS

| | | | |
|---|---|---|---|
| D. 376,848 | 12/1996 | Zellig et al. | D24/111 |
| 3,402,673 | 9/1968 | Ballentine et al. | 103/49 |
| 4,025,241 | 5/1977 | Clemens | 417/477 |

(List continued on next page.)

FOREIGN PATENT DOCUMENTS

| | | |
|---|---|---|
| 0 372 863 A2 | 6/1990 | European Pat. Off. |
| 0 569 030 A1 | 11/1993 | European Pat. Off. |
| WO 93/10853 | 6/1993 | WIPO |
| WO 93/25816 | 12/1993 | WIPO |
| WO 95/17913 | 7/1995 | WIPO |
| WO 96/27402 | 9/1996 | WIPO |
| WO 97/02059 | 1/1997 | WIPO |

OTHER PUBLICATIONS

Photographs of a pump product by Patient Solutions, Inc., Med–Mate™, Model 1100, pp. A1–A5.
Photographs of a pump product by Block Medical, Inc., a Hillenbrand Industry, Verifuse® Model No. B001500, pp. B1–B3.
Photographs of a pump product by Medfusion, Inc., a Medex, Inc. Company, Infu–Med™, WalkMed™ 440 PIC, pp. C1–C2.
Photographs of a pump product by C.R. Bard, Inc., Bard Medsystems Division, pp. D1–D3.
Photographs of a pump product by Pharmacia Deltec, Inc., pp. E1–E2.
Photographs of a pump product by AVI, Inc., AVID Guardian™ MICRO 10, pp. F1–F4.
Photographs of a pump product by Abbott Laboratories, Abbott/Shaw Life Care®Pump Model 3, pp. G1–G3.
Patient Soluctions, Inc., literature for MedMate™ 1100, 2 pages.
Patient Solutions, Inc. Directions for Use, MedMate™ Model 1100, 61 pages.
Block Medical, Inc. literature for Verifuse System, 1 page, date Nov. 1990.
Medfusion, Inc. Operations Manual for Medfusion Walk-Med™ Ambulatory Infusion Pump, 92 pages, dated Apr., 1990.
Medex Ambulatory Infusion Systems literature, entitled "WalkMed Pump Disposal Products," 2 pages, dated 1992.
Medex Ambulatory Infusion Systems literature, entitled "WalkMed PCA," 2 pages, dated 1993.
Bard Ambulatory PCA Pump literature, 2 pages, dated Jun., 1990.
Bard MedSystems Division, C.R. Bard, Inc., Quick Reference Guide, 2 pages, dated Feb., 1992.

(List continued on next page.)

*Primary Examiner*—Charles G. Freay
*Assistant Examiner*—Robert Z. Evora
*Attorney, Agent, or Firm*—Merchant & Gould P.C.

[57] ABSTRACT

A cassette for use with a pump control module includes a top surface configured for receipt of a tube and an access door. A method for using a pump control module includes mounting a cassette having a top surface comprising an access door to the pump control module; opening the access door; installing the tube into the cassette; closing the access door; and effecting pumping. A infusion pump comprising a pump control module and a cassette configured for receiving a tube, the cassette comprising an access door and a frame.

9 Claims, 4 Drawing Sheets

U.S. PATENT DOCUMENTS

| Patent # | Date | Inventor | Class |
|---|---|---|---|
| 4,187,057 | 2/1980 | Xanthopoulos | 417/63 |
| 4,236,880 | 12/1980 | Archibald | 417/478 |
| 4,394,862 | 7/1983 | Shim | 604/67 |
| 4,482,347 | 11/1984 | Borsanyi | 604/153 |
| 4,559,038 | 12/1985 | Berg et al. | 604/153 |
| 4,565,542 | 1/1986 | Berg | 603/131 |
| 4,585,399 | 4/1986 | Baier | 417/477 |
| 4,585,441 | 4/1986 | Archibald | 604/245 |
| 4,650,469 | 3/1987 | Berg et al. | 604/131 |
| 4,657,486 | 4/1987 | Stempfle et al. | 417/12 |
| 4,671,792 | 6/1987 | Borsanyi | 604/153 |
| 4,678,011 | 7/1987 | Weber | 138/96 |
| 4,684,364 | 8/1987 | Sawyer et al. | 604/123 |
| 4,689,043 | 8/1987 | Bisha | 604/250 |
| 5,017,059 | 5/1991 | Davis | 409/131 |
| 5,017,192 | 5/1991 | Dodge et al. | 604/250 |
| 5,074,756 | 12/1991 | Davis | 417/45 |
| 5,078,683 | 1/1992 | Sancoff et al. | 604/67 |
| 5,096,385 | 3/1992 | Georgi et al. | 417/18 |
| 5,105,983 | 4/1992 | Sancoff et al. | 222/103 |
| 5,106,366 | 4/1992 | Steppe | 604/30 |
| 5,165,874 | 11/1992 | Sancoff et al. | 417/474 |
| 5,207,642 | 5/1993 | Orkin et al. | 604/65 |
| 5,213,483 | 5/1993 | Flaherty et al. | 417/477 |
| 5,336,190 | 8/1994 | Moss et al. | 604/153 |
| 5,397,222 | 3/1995 | Moss et al. | 417/477.2 |
| 5,401,256 | 3/1995 | Stone et al. | 604/250 |
| 5,425,173 | 6/1995 | Moss et al. | 29/888.021 |
| 5,441,163 | 8/1995 | Carrasco | 220/23.86 |
| 5,482,438 | 1/1996 | Anderson et al. | 417/44.1 |
| 5,531,697 | 7/1996 | Olsen et al. | 604/131 |
| 5,564,915 | 10/1996 | Johnson | 417/572 |
| 5,632,394 | 5/1997 | Mecca et al. | 220/336 |
| 5,634,907 | 6/1997 | Rani et al. | 604/151 |
| 5,655,897 | 8/1997 | Neftel et al. | 417/477.2 |
| 5,658,252 | 8/1997 | Johnson | 604/131 |
| 5,788,671 | 8/1998 | Johnson | 604/131 |
| 5,791,880 | 8/1998 | Wilson | 417/14 |
| 5,823,746 | 10/1998 | Johnson | 417/53 |
| 5,879,144 | 3/1999 | Johnson | 417/474 |
| 5,954,485 | 9/1999 | Johnson et al. | 417/474 |

OTHER PUBLICATIONS

Bard MedSystems Division, C.R. Bard, Inc., Bard® Ambulatory PCA Pump Operation's Manual, 43 pages, dated Apr., 1990.

AVI, Inc. literature entitled "The AVI Advantage,", 2 pages, dated 1983.

AVI, Inc., literature, entitled "Bridging the Gap," 6 pages, dated Apr. 22, 1983.

Abbott Laboratories Hospital Products Division literature, entitled "The Blue Line System LifeCare®," 16 pages, dated Jul., 1990.

Abbott Laboratories Hospital Products Division literature, entitled "LifeCare® Electronic Flow Control Systems Catalog," 34 pages, dated May, 1985.

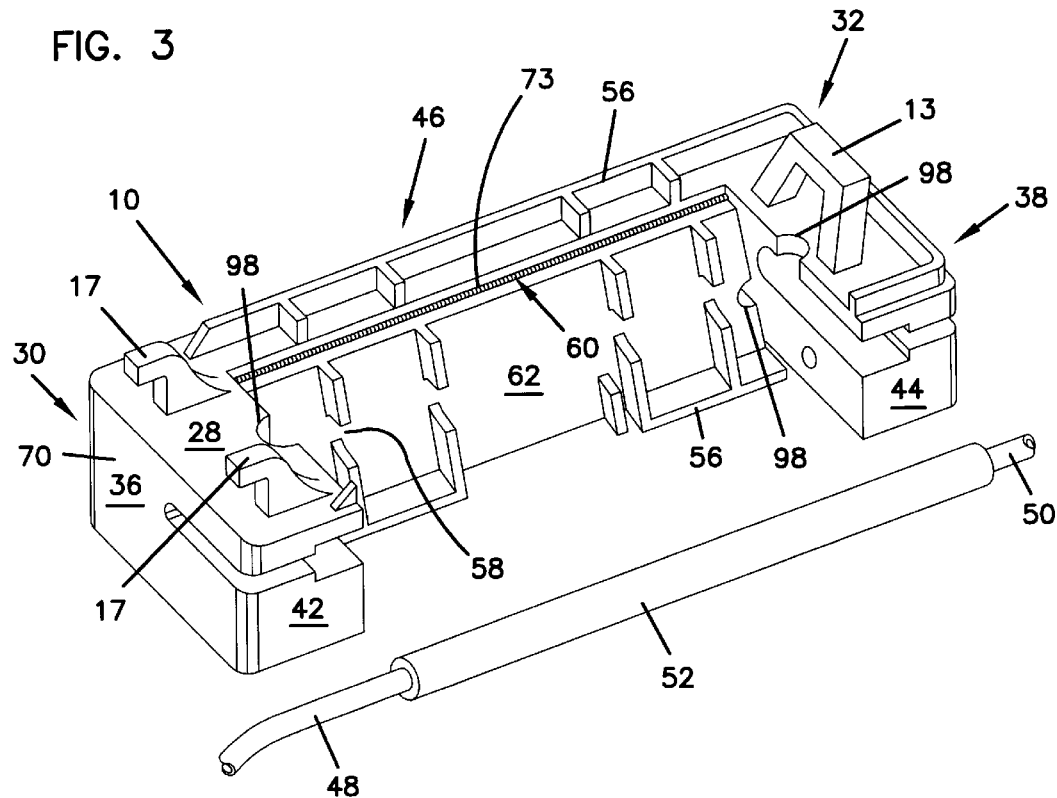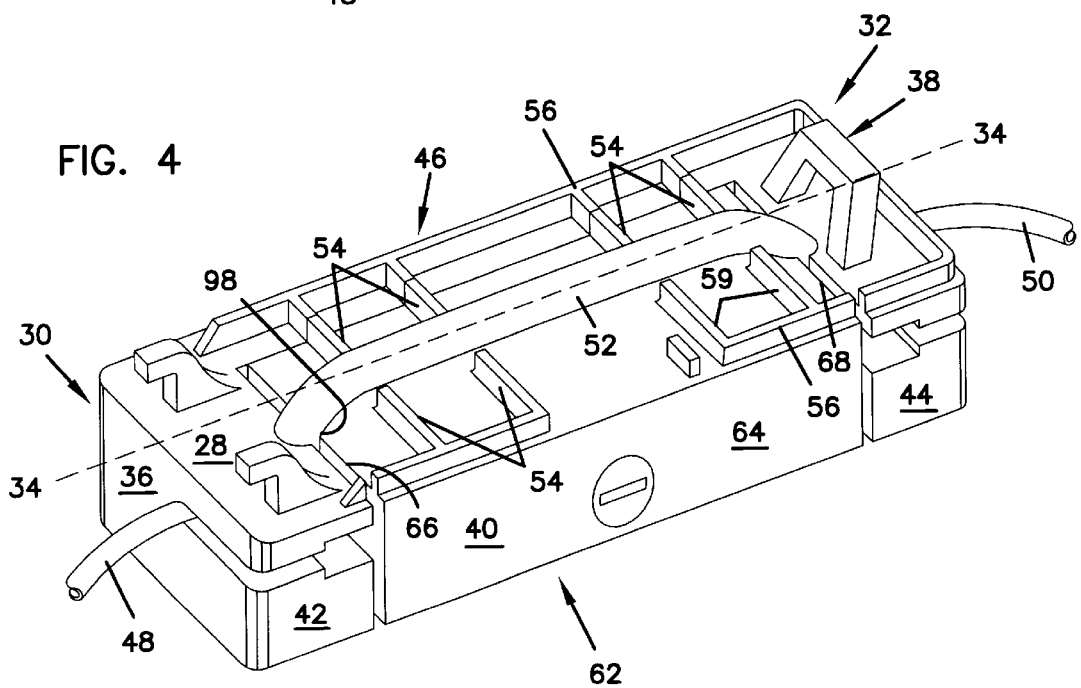

REUSABLE CASSETTE WITH A MOVEABLE DOOR

FIELD OF THE INVENTION

This invention relates generally to medical devices, and more particularly, to a reusable cassette having a moveable door for use with a pump control module and methods of use.

BACKGROUND OF THE INVENTION

In medical applications, fluid must sometimes be conveyed intravenously to a patient undergoing treatment. The fluid is usually contained in a fluid reservoir, typically a bag, conveyed through a tube, and injected into the patient's vein. Many times, regulating the volume and rate of fluid conveyed to the patient is advantageous, and in such instances, traditionally, infusion pumps are employed.

One such infusion pump effective for the application described above is disclosed in U.S. Pat. No. 4,559,038 ("the '038 patent") the entirety of which is herein incorporated by reference. The infusion pump disclosed and described therein regulates the conveyance of fluid from a fluid reservoir to a patient. In accordance with the infusion pump of the '038 patent, a fluid reservoir containing fluid for treating a patient is held in a cassette having a pressure plate immediately adjacent to a pump control module. A tube for conveying the fluid couples the fluid reservoir and the patient and provides a medium for conveying the fluid. A pump control module regulates the rate fluid is conveyed to the patient by applying physical pressure to the tube, thereby restricting the volume of fluid flow. In the '038 patent, the pump control module further comprises a pumping mechanism, having tube engaging members which engage and squeeze the tube against the pressure plate of the cassette. The tube engaging members include an expulser and an inlet valve and an outlet valve on opposite sides of the expulser.

A variation of the infusion pump described in the '038 patent includes a pump control module substantially as described above used in conjunction with a remote fluid reservoir, i.e., a fluid reservoir separate from the pump control module and the cassette. Typically, in infusion pumps incorporating remote fluid reservoirs, the fluid is still contained in the fluid reservoir, however, the fluid reservoir is secured on a holding apparatus, such as a pole, separate from the pump control module instead of in the cassette. The tube conveying the fluid from the remote fluid reservoir to the patient typically extends from the fluid reservoir, across the pump control module, and, to the patient.

In the past, due primarily to safety and hygiene concerns, cassettes were permanently attached to the tube, and when the fluid reservoir emptied or the patient's treatment was completed, the fluid reservoir, the tube, and the cassette were all discarded. Of course, disposing of the cassette contributes to waste and expense; therefore, reusable systems and methods which assist the operator replacing the fluid reservoir and expedite handling procedures associated with the system are desirable. The need for reusable cassettes and associated infusion pumps exists.

SUMMARY OF THE INVENTION

The present invention relates to a reusable cassette for use with a pump control module, usually in infusion pump systems. The cassette and pump control module function well as parts of a pumping system for regulating and conveying fluid from a fluid reservoir, through a tube, and finally to a patient. The cassette of the present invention is used with the pump control module to regulate and convey fluid from fluid reservoirs through tubes and can be reused with new tubes and/or fluid reservoirs. In this new system, while the fluid reservoir and the tube are generally disposed of after a single use, the cassette of the present invention is reusable. In addition to being reusable, the cassette of the present invention can remain secured to the pump control module while used tubes are removed and new tubes are installed into the infusion pump system.

The cassette of the present invention comprises an access door which is opened to remove used tubes and install new tubes without requiring that the cassette is detached from the control module. Once the tube is properly installed, the access door of the pressure plate is closed so that pumping can resume. When the access door is closed while a tube is installed within the cassette, the design of the cassette positions the tube properly so that the tube engaging members of the pump control module act on the tube and effect pumping.

BRIEF DESCRIPTION OF THE DRAWINGS

FIG. 3 is a perspective view of the cassette of FIG. 1, illustrating the access door in the open position, and a tube typically used with the present invention;

FIG. 4 is a perspective view of the cassette of FIGS. 1 and 3 showing the access door in the closed position and the tube installed into the cassette;

DETAILED DESCRIPTION OF THE PREFERRED EMBODIMENTS

Figure 1:
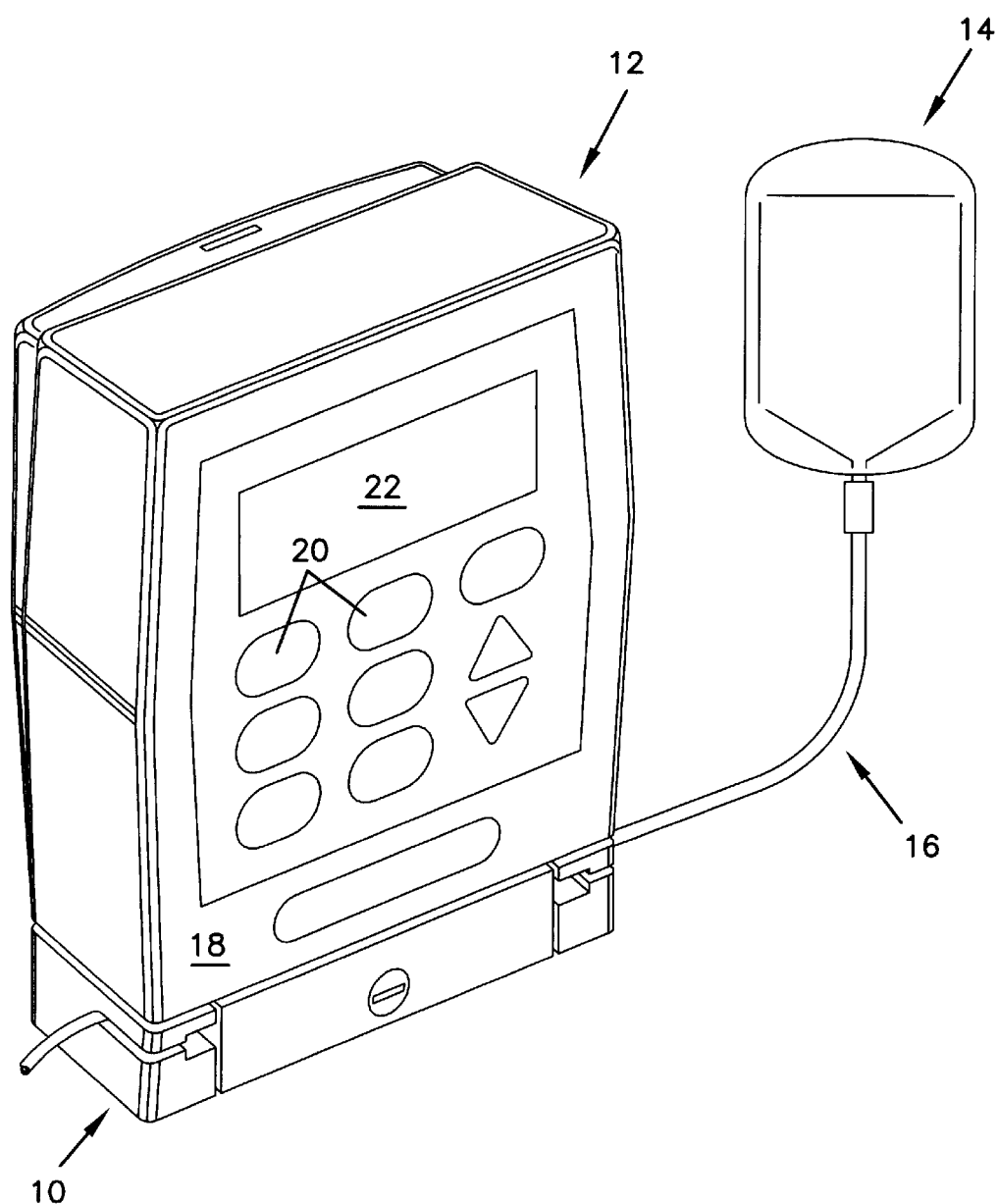
FIG. 1 is a perspective view of a preferred embodiment of a pump control module coupled to a cassette having a moveable access door.

This invention relates to a reusable cassette with a moveable access door suitable for supporting a tube extending from a fluid reservoir and used with a pump to deliver fluid to a patient. When properly positioned within the cassette, the tube is supported by a pressure plate of the cassette and held adjacent to tube engaging members of the pump so that pumping can be effected. This invention is directed to simplifying the process for replacing tubes and associated fluid reservoirs in infusion pump systems. The cassette is designed to be openable and closable in order to allow the user to remove a used tube and to replace it with a new tube without removing the cassette from the control module or having to use a new cassette each time the fluid reservoir and associated tube is replaced. One of the advantages of the present invention is that the cassette is reusable, and the tubes used with the pump control module can be removed and installed while the cassette remains secured to the pump control module. The tubes are replaced by opening the access door of the cassette, removing the used tube, installing a new tube, and closing the access door.

Reference will now be made in detail to preferred embodiments of the present invention wherein like reference numerals indicate like elements through the several views shown in FIGS. 1 through 5D. As embodied herein, a cassette is shown generally at 10 for use with a pump control module shown generally at 12. The pump control module 12 regulates the volume and rate fluid is conveyed from a fluid reservoir 14 through a tube 16 to a patient. The cassette 10 retains the tube 16 properly in position relative to tube engaging members 26 of the pump control module 12 so that fluid can be pumped.

Figure 2:
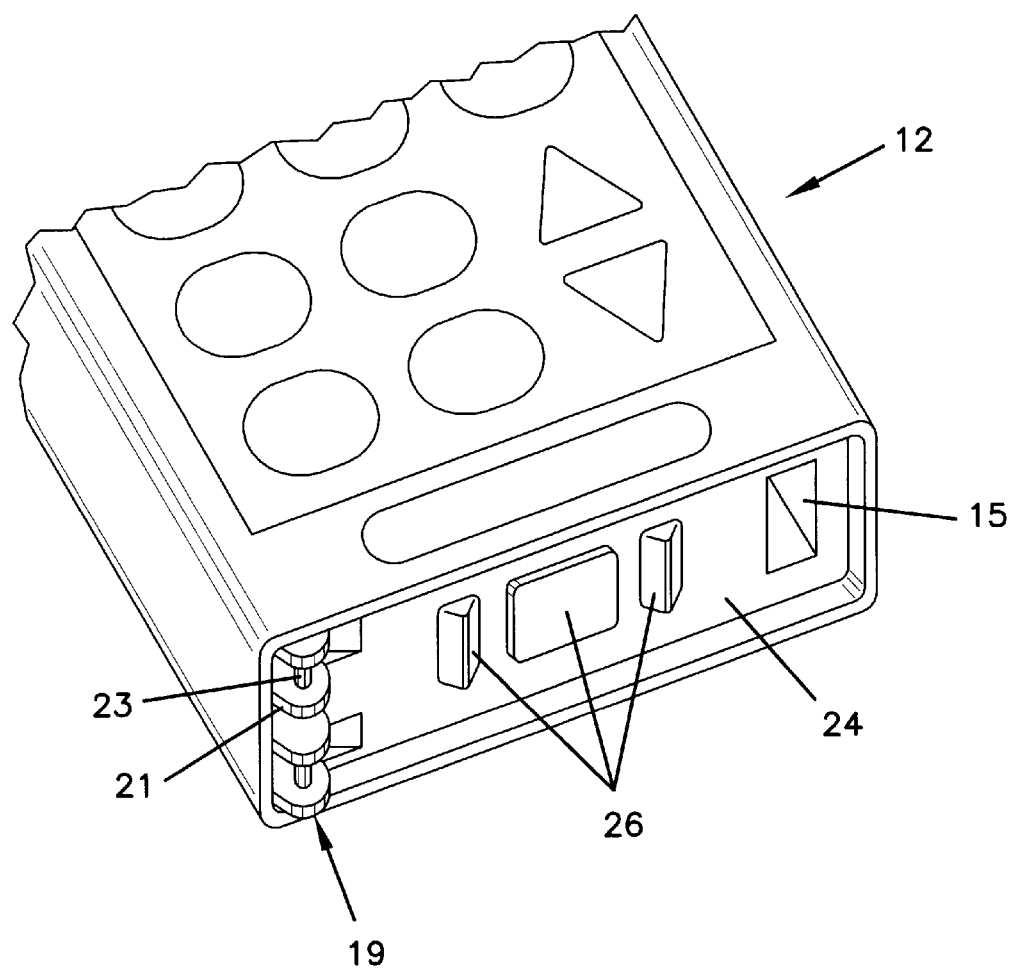
FIG. 2 is a perspective view of a tube interface region of the pump control module of FIG. 1.

In infusion pump systems such as this, the cassette 10 is sometimes secured to the control module 12 through the use of an anchor 13 incorporated into the cassette 10. The anchor 13 is preferably engaged by a releasable securing mechanism (not shown) inside a cavity 15 of the control module 12 of FIG. 2. The cassette 10 is additionally secured to control module 12 with at least one pump securing extension 17 as shown in FIGS. 3 and 4. The pump securing extensions 17 preferably engage a suspended pin assembly 19 or similar structure on the control module 12 as shown in FIG. 2. The pin assembly 19 usually comprises support structure 21 for retaining a pin 23.

Referring to FIG. 1, the pump control module 12 of the present invention preferably includes a control and display face 18. The control and display face 18 of the present invention comprises a plurality of control keys 20 for operating the pump control module 12 and a display 22 for conveying input and output information to the pump system operator. While most embodiments of the present invention incorporate displays 22 which convey information in digital form, those of ordinary skill in the art will recognize that some alternative displays 22 function equally well.

A tube interface region 24, as best shown in FIG. 2, is preferably positioned substantially orthogonal to the control and display face 18 on the pump control module 12 of the present invention. The tube interface region 24 preferably comprises the tube engaging members 26 which apply mechanical pressure to the tube 16, thereby, regulating the volume and rate fluid is conveyed from the fluid reservoir 14 to the patient. When the cassette 10 is properly secured to the control module 12 while the tube 16 is properly positioned, the tube engaging members 26 selectively occlude the tube 16 to effect pumping, while at the same time preventing free flow. U.S. Pat. No. 4,559,038, noted above, includes a similar tube interface region with three tube engaging members.

As shown in FIGS. 3 and 4, the cassette 10 includes atop surface 28, which acts as a tube supporting surface, having a first end 30 and a second end 32. In the embodiment of the present invention of FIGS. 3 and 4, the cassette 10 receives the portion of the tube 16 extending from the fluid reservoir 14 at the second end 32 and receives the portion of the tube 16 leading to the patient at the first end 30. As best illustrated in FIG. 4, when the tube 16 is properly installed in the cassette 10 of the present invention, the tube 16 preferably extends along a longitudinal centerline 34 of the top surface 28 of the cassette 10 between the first end 30 and the second end 32. A first end surface 36 and a second end surface 38 are preferably adjacent the first end 30 and the second end 32 of the cassette 10, respectively, and extend downward from the top surface 28 of the cassette 10.

A front door surface 40, a first front frame surface 42, and a second front frame surface 44, shown in FIG. 4, are disposed between the first end surface 36 and the second end surface 38 and extend downward from the top surface 28 of the cassette 10. The front door surface 40, the first front frame surface 42, and the second front frame surface 44 together approximately equal the length of the cassette 10 (length from the first end 30 to the second end 32 of the cassette 10). A rear surface 46, preferably substantially parallel to the front door surface 40, the first front frame surface 42, and the second front frame surface 44, completes the border around the top surface 28 of the cassette 10. In the embodiment of the present invention depicted in FIGS. 1, 3, and 4 the length of the rear surface 46 approximately equals to the sum of the lengths of the front door surface 40, the first front frame surface 42, and the second front frame surface 44.

The tube 16 used with preferred embodiments of the present invention includes a first small diameter portion 48, a second small diameter portion 50, and a larger diameter engaging portion 52 disposed in between as shown in FIG. 3. Typically, the larger diameter engaging portion 52 of the tube 16 is of relatively larger inner diameter than the first small diameter portion 48 and the second small diameter portion 50 of the tube 16. The larger diameter engaging portion 52 of the tube 16 is preferably aligned with the top surface 28 of the cassette 10 when the tube 16 is properly installed in the cassette 10. As shown in FIG. 4, the larger diameter engaging portion 52 of the tube 16 lies substantially along the longitudinal centerline 34 of the top surface 28 of the cassette 10. The larger diameter engaging portion 52 of the tube 16 is the portion of the tube 16 designed to be engaged by the tube engaging members 26 of the pump control module 12.

A plurality of tube centering ribs 54 preferably extend substantially laterally across the top surface 28 of the cassette 10. Front and rear rails 56 extend along the front door surface 40 and/or along the rear surface 46 of the cassette 10. The plurality of ribs 54 and the rails 56 are preferably molded, or otherwise integrated, into the top surface 28 of the cassette 10 and provide additional structural support to the cassette 10.

In the embodiment of the cassette 10 shown in FIGS. 3 and 4, the height of each of the plurality of ribs 54 is substantially the same as the height of the rails 56. The height of the plurality of ribs 54 and the rails 56 is preferably uniform and facilitates the pumping action between the tube engaging members 26 of the pump control module 12 and the larger diameter engaging portion 52 of the tube 16. The rails 56 are continuous and extend along the rear surface 46, along the second end surface 38, along the second front frame surface 44, and along the front door surface 40.

Each of the plurality of ribs 54 preferably extends substantially laterally across the top surface 28 of the cassette 10, nearly to the longitudinal centerline 34 of the cassette 10, substantially as shown in FIG. 4. The plurality of ribs 54 are spaced to avoid interfering with the tube engaging members 26 of the pump control module 12. With reference to FIGS. 3 and 4, the plurality of ribs 54 define gaps 58 for receiving the larger diameter engaging portion 52 of the tube 16 when positioned in the cassette 10. The plurality of ribs 54 guide and retain the larger diameter engaging portion 52 of the tube 16 to permit the tube engaging members 26 of the pump control module 12 to effect pumping.

An access door 62 to facilitate the installation and removal of the tube 16 is preferably incorporated in the cassette 10 of the present invention. A swinging front 64 of the access door 62 is preferably adjacent the front door surface 40 of the cassette 10. A hinged rear 60 of the access door 62 is preferably located between the rear surface 46 of the cassette 10 and the longitudinal centerline 34 of the top surface 28 of the cassette 10. The length of the access door 62 is preferably substantially the same as the length of the front door surface 40, and the access door 62 is located between the first front frame surface 42 and the second front frame surface 44.

The access door 62 is further defined by a first side door perimeter 66 and a second side door perimeter 68, both of which extend between the hinged rear 60 and the swinging front 64 adjacent the first front frame surface 42 and the second front frame surface 44, respectively.

The hinged rear 60 of the access door 62 is preferably pivotally coupled to a frame 70 of the cassette 10 of the present invention. One method of coupling the access door 62 to the frame 70 at the hinged rear 60 comprises simple hinges 73 affixed to the underside of the top surface 28 at a junction 72 of the hinged rear 60 of the access door 62 and the frame 70 of the cassette 10. The frame 70 of the cassette 10 comprises the portions of the cassette 10 not within the perimeter of the access door 62. Thus, the frame 70 of the cassette 10 is the area of the cassette 10 not located within the swinging front 64, the hinged rear 60, the first side door perimeter 66, and the second side door perimeter 68 of the access door 62.

The access door 62 of the present invention has essentially two positions—open and closed. When the access door 62 is open, substantially as shown in FIG. 3, the swinging front 64 of the access door 62 is pivoted downward and the top surface 28 of the access door 62 forms an angle with the top surface 28 of the frame 70 of the cassette 10. While the access door 62 is open, the tube 16 can be installed and/or removed from the cassette 10.

When the access door 62 is closed, as best shown in FIG. 4, the tube 16 is properly positioned for the tube engaging members 26 of the pump control module 12 to engage the larger diameter engaging portion 52 of the tube 16 to effect pumping and convey fluid from the fluid reservoir 14 to the patient.

Figure 5A:
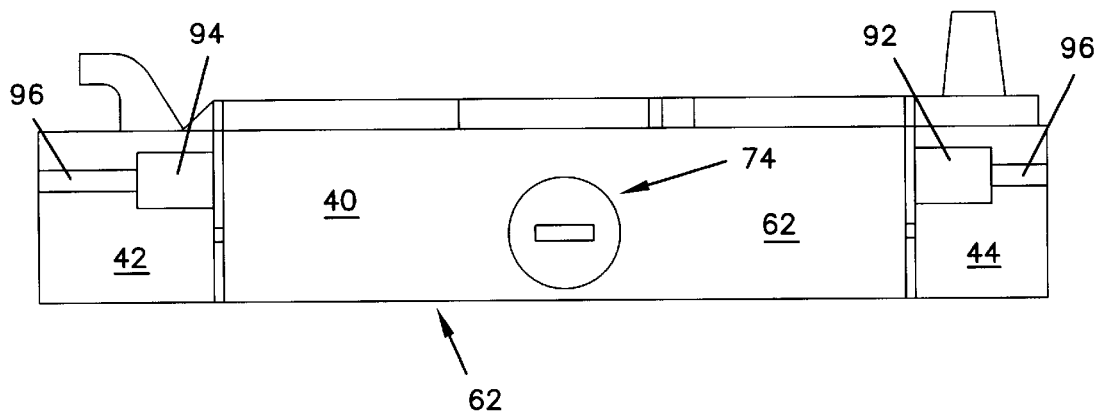
FIG. 5A is a front view of the cassette.
Figure 5B:
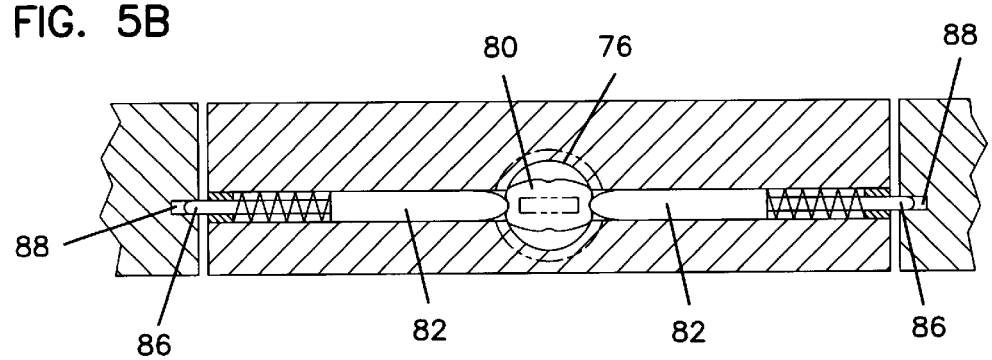
FIG. 5B is a cross-sectional front view of the locking mechanism of the cassette FIG. 5A in the locked position and illustrating a cam, locking pins, springs, and recesses.
Figure 5C:
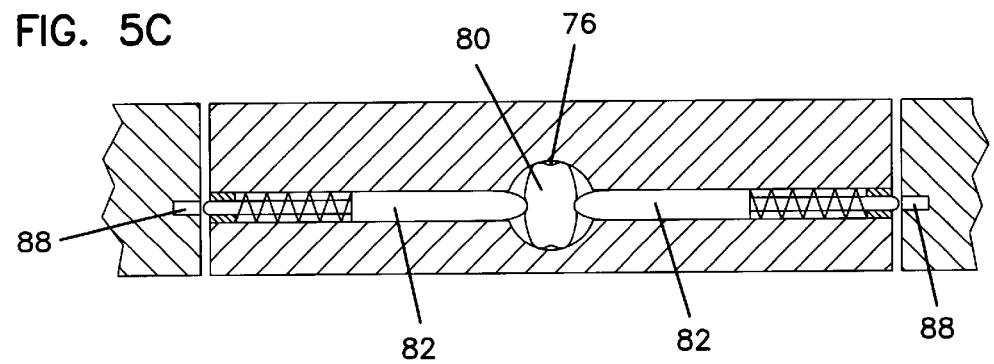
FIG. 5C shows the locking mechanism of FIG. 5B in the unlocked position.
Figure 5D:
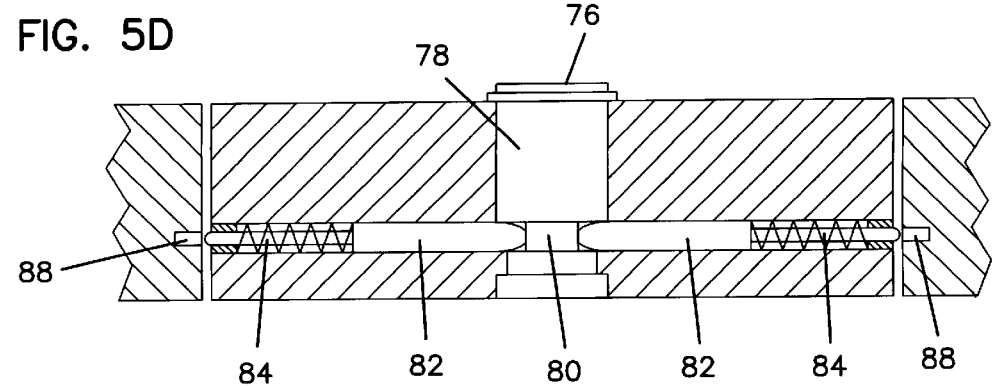
FIG. 5D is a cross-sectional top view of the access door of the locking mechanism of FIG. 5C.

Referring to the series of illustrations of FIGS. 5A through 5D, the locking mechanism 74 of one preferred embodiment of the present invention is shown FIG. 5A shows the front door surface 40 of the cassette 10 while the access door 62 is in the closed position. A rotatable latch 76 is preferably located in an accessible position on the front door surface 40 of the cassette 10. The locking mechanism 74 preferably comprises the rotatable latch 76, a core 78, a cam 80, at least one locking pin 82 which interacts with the cam 80 as a cam follower, and at least one spring 84 to maintain pressure on the locking pin 82. As shown in increased detail in FIG. 5B, when the access door 62 is closed and in the locked position, distal ends 86 of the locking pins 82 are retained in recesses 88 formed in the frame 70 of the cassette 10. When the latch 76 is rotated and the locking mechanism 74 is unlocked, as shown in FIG. 5C, the cam 80 rotates, and proximal ends 90 of the locking pins 82 follow the cam 80, thereby freeing the distal ends 86 of the locking pins 82 from the recesses 88 of the frame 70 of the cassette 10. FIG. 5D is a cross-sectional view of the locking mechanism 74 in the unlocked position of FIG. 5C. In further embodiments, a more secure locking mechanism can be provided which is only operable with a specially shaped tool or key.

For the purpose of accommodating the tube 16 when installing in the cassette 10, the second front frame surface 44 has an inlet tube slot 92 through which the second small diameter portion 50 of the tube 16 extending from the fluid reservoir 14 passes leading to the tube engaging members 26 of the pump control module 12. The inlet tube slot 92 is preferably an elongated channel 96 extending from the second end 32 of the cassette 10, along the second front frame surface 44, and to the second side door perimeter 68 of the access door 62 of the cassette 10. The height of the inlet tube slot 92 is preferably greater nearer the access door 62 to accommodate the larger diameter engaging portion 52 of the tube 16 and narrower nearer the second end surface 38 to accommodate the second small diameter portion 50 of the tube 16.

Further, in some embodiments of the present invention, the first front frame surface 42 has an outlet tube slot 94 through which the first small diameter portion 48 of the tube 16 passes the tube 16 is installed in the cassette 10. The outlet tube slot 94, like the inlet tube slot 92 described above, is preferably the elongated channel 96 extending from the first side door perimeter 66 of the access door 62 of the cassette 10, through the first front frame surface 42, and to the first end surface 36 of the cassette 10. The height of the outlet tube slot 94 is preferably greater nearer the access door 62. The relative sizing of the tube 16 used with some embodiments of the present invention prevents the tube 16 from being inadvertently or improperly removed from the cassette 10 by longitudinal pull, accidental or otherwise.

The elongated channels 96 of the inlet tube slot 92 and the outlet tube slot 94 are substantially parallel to the top surface 28 of the access door 62 in some embodiments of the present invention and, in other embodiments, the inlet tube slot 92 and the outlet tube slot 94 are inclined in a upward direction as the elongated channels 96 approach the longitudinal centerline 34 of the cassette 10. One advantage of inclining the elongated channels 96 upward is that the larger diameter engaging portion 52 of the tube 16 is urged closer to the top surface 28 of the cassette 10.

Indentations 98 are located in the access door 62 and/or the frame 70 to permit the larger diameter engaging portion 52 of the tube 16 to reach from the inlet tube slot 92 up to the gaps 58 located along the top surface 28 of the access door 62 and into the outlet tube slot 94 without being crimped by the first side door perimeter 66 or the second side door perimeter 68. The indentations 98 are preferably sized such that the tube 16 does not crimp when installed in the cassette 10 when the access door 62 is closed; therefore, flow is not inhibited.

In operation, the tube 16 is installed into the cassette 10 as follows: when the pump is not operating, the access door 62 of the cassette 10 is opened by releasing the locking mechanism 74. The access door 62 is maintained open while first small diameter portion 48 and the second small diameter portion 50 of the tube 16 are slid into the inlet tube slot 92 and the outlet tube slot 94, respectively. The larger diameter engaging portion 52 of the tube 16 is preferably substantially centered along the longitudinal centerline 34 and placed into the gaps 58 formed by the plurality of ribs 54 on the top surface 28 of the cassette 10. The access door 62 of the cassette 10 is then closed. If securing the access door 62 requires an additional step, such as rotating the latch 76 of the locking mechanism 74 as in the embodiment of FIG. 5, that additional step is performed.

In some embodiments of the present invention, the cassette 10 is constructed of material which ensures secure mounting to the pump control module 12 and proper fluid conveyance. The material or materials selected preferably withstand repeated reuses with the pump control module 12 a suitable number of times and also allow the pump control module 12 to convey fluid properly without free flow or without requiring excessive energy drain and/or causing a stoppage of the pumping mechanism. All metal, molded plastic with metal reinforcement, and glass-filled plastic are possible constructions for a reusable cassette. Those of ordinary skill in the art will recognize a number of materials exist which will perform sufficiently.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A cassette for use with a pump control module, the cassette comprising:

a top surface configured for receipt of a tube having a first end including at least one pump securing extension and a second end including an anchor, and a center section therebetween;

a frame interconnecting the first end to the second end; and a hingedly moveable access door mounted to the frame disposed in the center section of the top surface.

2. The cassette of claim 1, wherein the access door is mounted to the frame of the cassette with at least one hinge.

3. The cassette of claim 1, wherein the top surface comprises a plurality of ribs forming gaps to receive the tube.

4. The cassette of claim 1, wherein the frame further comprises an inlet tube slot and an outlet tube slot.

5. The cassette of claim 1, wherein the access door further comprises a locking mechanism.

6. The cassette of claim 5, wherein the locking mechanism comprises a cam and at least one cam follower.

7. The cassette of claim 6, wherein the cam follower is a locking pin.

8. A cassette for use with a pump control module, the cassette comprising:

a first portion having a first end including at least one pump securing extension and a second end including an anchor, and defining a center open section therebetween;

a second moveable portion hingedly mounted to the first portion, the second moveable portion including a top surface communicating with the center open section of the first portion, the top surface including a plurality of ribs forming gaps to receive a tube; and a locking mechanism for selectively locking the second moveable portion to the first portion.

9. The cassette of claim 8, wherein the gaps are aligned in a direction between the first and second ends of the first portion.

* * * * *